(12) United States Patent
Torrie

(10) Patent No.: US 8,556,916 B2
(45) Date of Patent: Oct. 15, 2013

(54) METHOD AND DEVICE FOR SUTURE MANIPULATION

(75) Inventor: Paul Alexander Torrie, Marblehead, MA (US)

(73) Assignee: Smith & Nephew, Inc., Andover, MA (US)

( * ) Notice: Subject to any disclaimer, the term of this patent is extended or adjusted under 35 U.S.C. 154(b) by 133 days.

(21) Appl. No.: 13/027,003

(22) Filed: Feb. 14, 2011

(65) Prior Publication Data

US 2012/0209300 A1    Aug. 16, 2012

(51) Int. Cl.
*A61B 17/04* (2006.01)

(52) U.S. Cl.
USPC ............................................................ 606/148

(58) Field of Classification Search
USPC ...................................... 606/148, 139, 144
See application file for complete search history.

(56) References Cited

U.S. PATENT DOCUMENTS

| | | | |
|---|---|---|---|
| 5,201,741 | A | 4/1993 | Dulebohn |
| 5,336,239 | A | 8/1994 | Gimpelson |
| 5,391,170 | A | 2/1995 | McGuire et al. |
| 5,443,509 | A | 8/1995 | Boucher et al. |
| 5,499,991 | A | 3/1996 | Garman et al. |
| 5,658,289 | A | 8/1997 | Boucher et al. |
| 5,772,672 | A | 6/1998 | Toy et al. |
| 5,904,692 | A | 5/1999 | Steckel et al. |
| 6,485,504 | B1 | 11/2002 | Johnson et al. |
| 2002/0156344 | A1 | 10/2002 | Pasricha et al. |
| 2003/0078585 | A1 | 4/2003 | Johnson et al. |
| 2004/0127915 | A1 | 7/2004 | Fleenor et al. |
| 2004/0249393 | A1 | 12/2004 | Weisel et al. |
| 2005/0021052 | A1 | 1/2005 | Kim |
| 2005/0251178 | A1 | 11/2005 | Tirabassi et al. |
| 2006/0036265 | A1 | 2/2006 | Dant |
| 2006/0069399 | A1 | 3/2006 | Weisel et al. |
| 2007/0010829 | A1 | 1/2007 | Nobles et al. |
| 2007/0038230 | A1 | 2/2007 | Stone et al. |
| 2008/0114378 | A1 | 5/2008 | Matsushita |
| 2008/0234729 | A1 | 9/2008 | Page et al. |
| 2008/0255591 | A1 | 10/2008 | Harada et al. |
| 2009/0018554 | A1 | 1/2009 | Thorne et al. |
| 2009/0069824 | A1 | 3/2009 | Chu |
| 2009/0069845 | A1 | 3/2009 | Frushell et al. |
| 2009/0082787 | A1 | 3/2009 | Pang |
| 2009/0198274 | A1 | 8/2009 | Frushell et al. |
| 2010/0076440 | A1 | 3/2010 | Pamichev et al. |
| 2010/0268241 | A1 | 10/2010 | Flom et al. |
| 2010/0312179 | A1 | 12/2010 | Nikolchev et al. |

FOREIGN PATENT DOCUMENTS

JP     2007050200 A     3/2007

OTHER PUBLICATIONS

Invitation to pay additional fees re: International Applic. PCT/US2012/024827 & communication re: results of the partial international search, mailed on May 10, 2012.

*Primary Examiner* — Darwin Erezo
*Assistant Examiner* — Shaun L David
(74) *Attorney, Agent, or Firm* — Pierce Atwood LLP; Joseph M. Maraia

(57) ABSTRACT

The invention relates to a suture manipulation device. The suture manipulation device includes a body and a snare. The snare is operatively connected to the body and is adapted to protract from the body, and after protracting from the body, rotate independent of the body. The snare is further adapted to ensnare a portion of suture passed through tissue while rotating, and secure the portion of the suture.

10 Claims, 14 Drawing Sheets

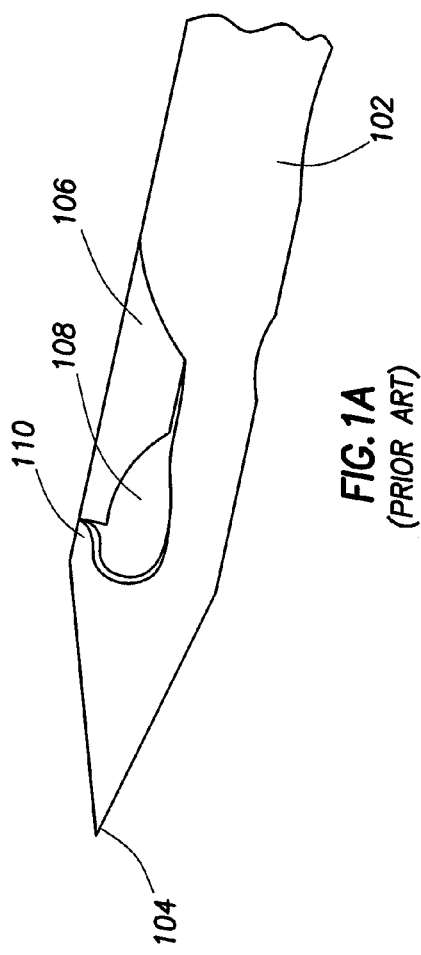
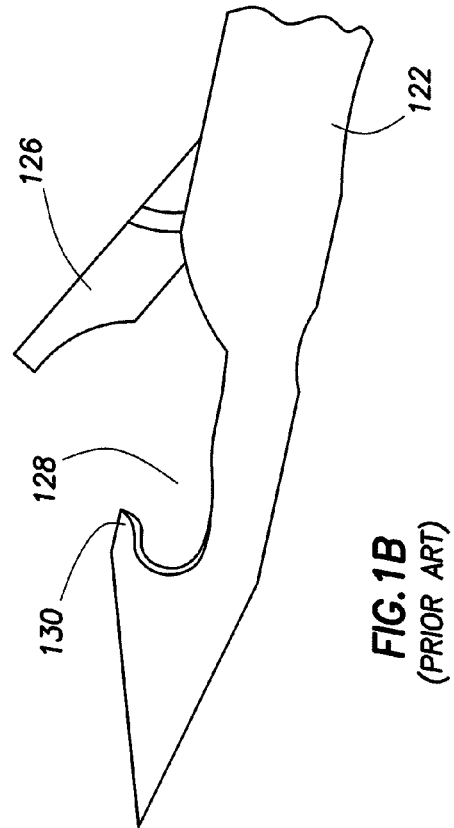

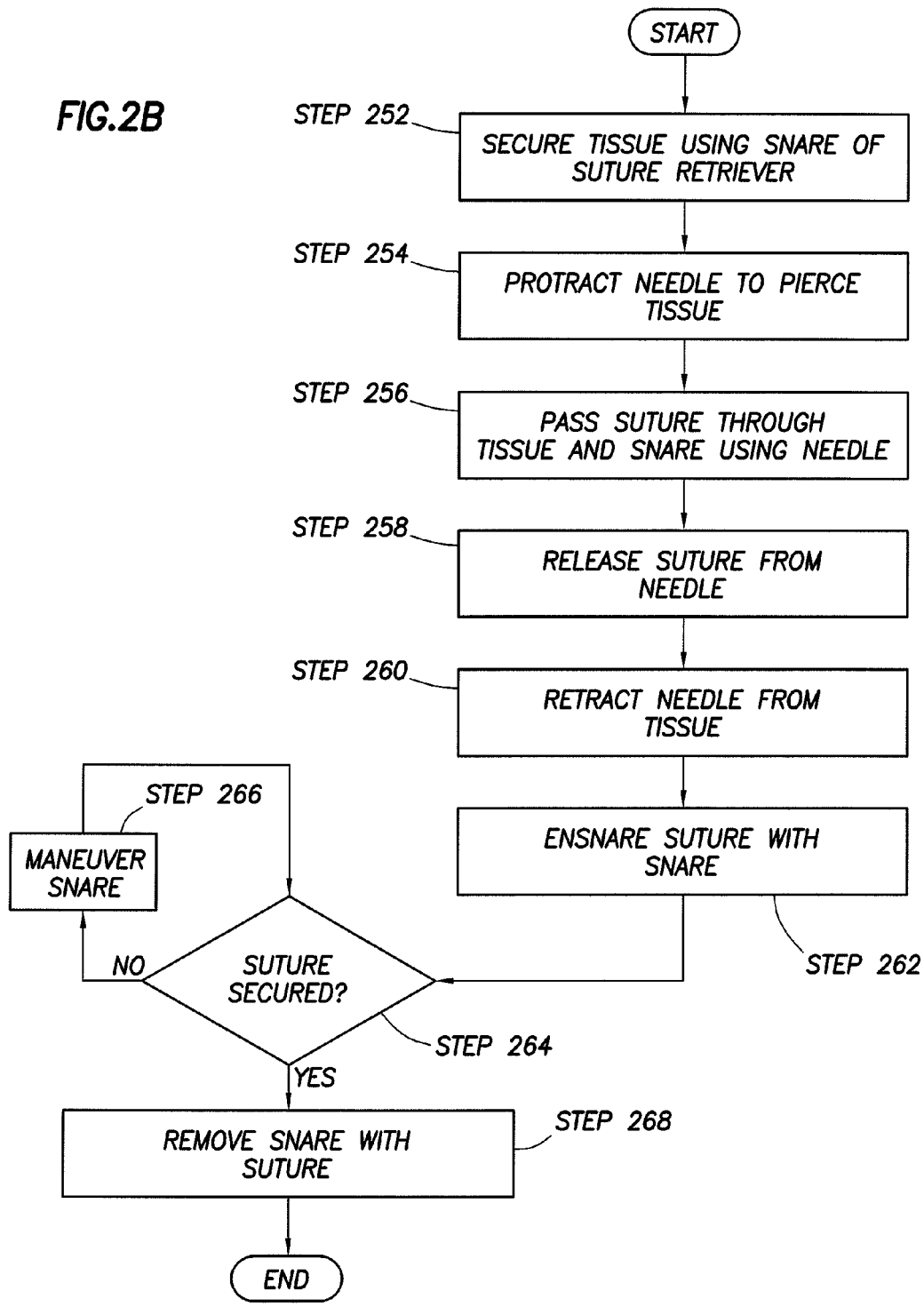

METHOD AND DEVICE FOR SUTURE MANIPULATION

BACKGROUND

In surgical applications, suture is passed through tissue to close wounds or surgical incisions. The suture holds one or more tissues together for a period of time. Because of constrained and sometimes inflexible spaces in which to work, surgeons and other medical personnel must use specialized tools to apply suture to a wound. Specifically, suture manipulation such as puncturing tissue to release suture and/or retrieving suture to complete a stitch requires specialized tools.

SUMMARY

In general, in one aspect, the invention relates to a suture manipulation device. The suture manipulation device includes a body and a snare. The snare is operatively connected to the body and is adapted to (1) protract from the body, (2) rotate, after protracting from the body, independent of the body, (3) ensnare a portion of suture passed through tissue while rotating, and (4) secure the portion of the suture.

In general, in one aspect, the invention relates to a suture manipulation device. The suture manipulation device includes a snare with a receiving end that is adapted to (1) provide support to tissue, (2) ensnare a portion of suture passed through the tissue and the receiving end, (3) remove the support of the tissue, (4) secure, while removing the support of the tissue, the portion of the suture using the receiving end, and (5) remove, using the receiving end, the portion of the suture.

In general, in one aspect, the invention relates to a method for manipulating a suture. The method involves (1) protracting a snare from a body of a suture manipulation device, (2) rotating the snare independent of the body of the suture manipulation device, (3) ensnaring a portion of the suture with the snare while rotating the snare, and (4) securing the portion of the suture.

In general, in one aspect, the invention relates to a method for manipulating a suture. The method involves (1) providing support to tissue using a snare of a suture manipulation device, (2) ensnaring, using the snare and without moving the snare, a portion of the suture when the portion of the suture passes through the tissue and is released by a needle, (3) securing, while removing the support to the tissue, the portion of the suture with the snare, and (4) removing the snare with the portion of the suture from the tissue.

Other aspects of the invention will be apparent from the following description and the appended claims.

BRIEF DESCRIPTION OF DRAWINGS

FIGS. 1A and 1B show a suturing tool, known in the art, adapted to remove a suture.

FIGS. 2A and 2B each show a flowchart of a method in accordance with one or more embodiments of the invention.

DETAILED DESCRIPTION

Figure 2A:
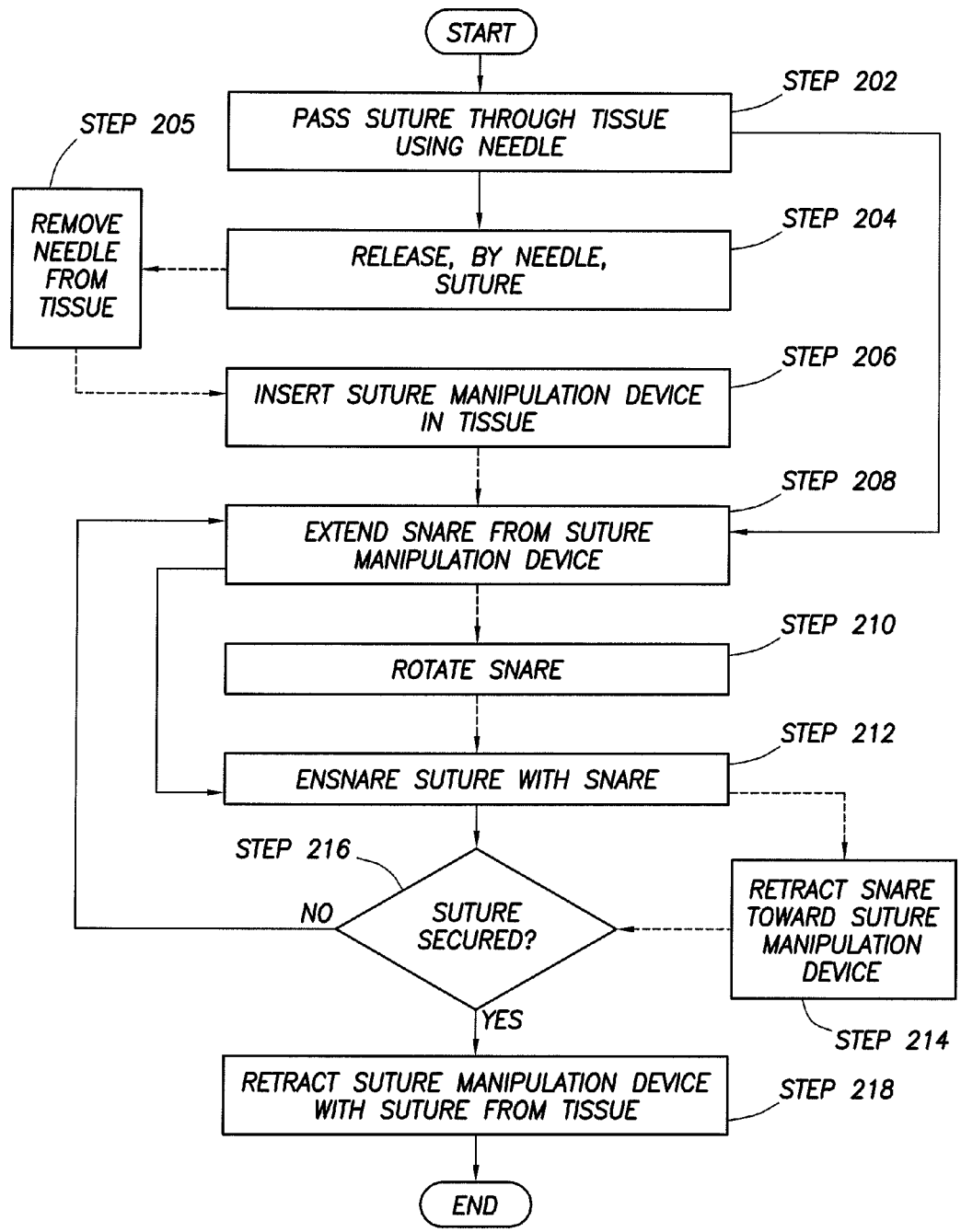

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention describe a method and device for suture manipulation. Specifically, one or more embodiments of the invention protract a snare from a body of a suture manipulation device. Once protracted, the snare rotates independent of the body of the suture manipulation device to ensnare a portion of the suture. The snare then secures the portion of the suture. In one or more embodiments of the invention, a pushrod, located in a cavity of the body of the suture manipulation device, is used to control the snare. When a pushrod is retracted, the snare may also be retracted. A pushrod may also rotate independent of the body of the suture manipulation device. For example, the suture manipulation device itself may not rotate when the snare does, whether controlled by the pushrod, for example in the ensnarement of a suture. As used herein, suture may refer to suture thread.

In one or more embodiments of the invention, manipulation of a suture may involve pushing a suture through tissue, moving a suture, dropping a suture (i.e., releasing the suture, at least in part, from a needle), retrieving a suture, extracting a suture, and/or otherwise moving a suture. As used herein, the suture manipulation device may be a suture pusher, a suture shuttle, a suture retriever, and/or any other suitable device for manipulating a suture. In other words, the suture manipulation device may be configured to manipulate a suture and/or a shuttle. As used herein, a suture may be permanent (i.e., used to create a stitch) or temporary (e.g., a shuttle that is pushed through tissue, where an end of the shuttle is tied to a permanent suture used to create a stitch).

Embodiments of the invention are designed to support the creation of one or more stitches. A stitch uses a suture to hold one or more materials in place over a period of time. A stitch is created when a suture is inserted into and pushed through (i.e., passed through) tissue. Tissue may include, but is not limited to, epithelial and other layered covering tissue (e.g., the outer layer of skin, and tissue surrounding internal organs such as the liver), connective tissue (e.g., inner layer of skin, tendons, ligaments, cartilage, bone, fat), muscle tissue, and nerve tissue. A suture may be any suture used in surgical and other similar procedures. For example, a suture may range in size from #11/0 United States Pharmacopeia (USP) to #7 USP. Further, a suture may be made from a number of materials, including but not limited to silk, catgut, polyglycolic acid, polyactic acid, polydioxanone, nylon, and polypropylene. Embodiments of the invention may be used to manipulate (e.g., push, ensnare, secure, extract) suture inside a body (e.g., human, animal) and/or external to the body (as with a surface wound).

As used herein, the term distal means the most distant point. Also, the term proximal means the closest point. The perspective from which distal and proximal are described herein is an operator of a tool having one or more components. Specifically, embodiments of the invention describe a device (e.g., a suture retriever, a suture shuttle) used in surgical applications to stitch a wound or other opening of tissue. The distal end describes the end of the device (or component of the device) closest to the tissue (i.e., furthest away from a user of the device). Likewise, the proximal end describes the end of the device (or component of the device) closest to the user of the device (i.e., furthest away from the tissue). Also, as used herein, a user may be any person creating stitches in tissue, including but not limited to a surgeon, a nurse, a technician, or a veterinarian.

FIGS. 1A and 1B show a suture manipulation device (e.g., a suture retriever) known in the art. As shown in FIG. 1A, the suture manipulation tool includes a shaft (102), a pointed end (104), and a clamping arm (106) that yields a gap (108) between a portion of the shaft (102) and the underside of the clamping arm (106). The end of the clamping arm (106) may be joined against a notch (110) in the shaft (102) when the clamping arm (106) is in a closed position. The clamping arm (106) shown in FIG. 1A is in a closed position, which may be used when inserting the suture manipulation device into an area to manipulate a suture. The material with which the shaft (102), the pointed end (104) (e.g., a needle), and the clamping arm (106) are made from may be the same or one or more different materials. The suture manipulation device may be made for repeated use, or for temporary (e.g., one time) use.

FIG. 1B shows the suture manipulation device of FIG. 1A where the clamping arm (126) is in an open position. Specifically, the clamping arm (126) is in an open position to secure a suture. The clamping arm (126) may be opened in one of a number of ways, including release of a latch, applying pressure on a hinge, or some other suitable mechanism. The mechanism used to open the clamping arm may be located at one or more locations, including but not limited to the hinge of the clamping arm (126) to the body (122) and the notch (130). When the clamping arm (126) is open, the gap (128), combined with the notch (130), may be used to capture the suture.

A suture manipulation device, as described above with respect to FIGS. 1A and 1B, may be configured to manipulate (e.g., pass, drop, retrieve) a suture and/or a suture shuttle. An example of suture manipulation devices known in the art includes, but is not limited to, the ACCU-PASS® suture shuttles. (ACCU-PASS® is a registered trademark of Smith & Nephew, Inc. of Memphis, Tenn.)

FIGS. 2A and 2B each show a flowchart of a method for manipulating a suture in accordance with one or more embodiments of the invention. While the various steps in these flowcharts are presented and described sequentially, some or all of the steps may be executed in different orders, may be combined or omitted, and some or all of the steps may be executed in parallel. Further, in one or more of the embodiments of the invention, one or more of the steps described below may be omitted, repeated, and/or performed in a different order. In addition, additional steps, omitted in FIGS. 2A and 2B, may be included in performing these methods. Accordingly, the specific arrangement of steps shown in FIGS. 2A and 2B should not be construed as limiting the scope of the invention.

Referring to FIG. 2A, one method for manipulating a suture in accordance with one or more embodiments of the invention is described. In Step 202, a suture is passed through tissue using a needle. The needle may be part of a suture manipulation device without suture retrieving capability or a suture manipulation device with suture retrieving capability. A suture manipulation device may be any device capable of puncturing (i.e., piercing) the tissue and securing the suture as the suture manipulation device, along with the suture, is pushed beyond the tissue. The suture manipulation device may include a penetrating component (i.e., needle) at the distal end. The needle of the suture manipulation device may be straight or curved. A cross section of the needle may be circular, oval, or any other suitable shape. The needle may have a diameter (or length of a major axis) that may be as small as 1 mm (or less) or as large as 2.5 mm (or larger). The size of the needle may depend on the size (e.g., diameter) of the suture. The needle may be several inches long and have a proximal end that attaches to a body that may include a handle.

In Step 204, the suture is released by the needle. In one or more embodiments of the invention, the suture may be released from the needle using natural forces. For example, if the needle is extended a distance (e.g., one inch) beyond the tissue and snare, friction created by elements within the body receiving the suture may be adequate to release the suture from the needle as the needle retracts. The suture may also be released from the suture manipulation device using some control. The control may be manual (e.g., a user pressing a button) or automatic (e.g., the suture is released after the suture manipulation device travels five millimeters past the tissue). Also, the control may be located on the suture manipulation device (e.g., on the handle of the suture manipulation device) or remote from the suture manipulation device (e.g., remote control). As an example, the suture manipulation device may include a snare (e.g., a hook) that holds the suture in a retracted position when the suture manipulation device penetrates and traverses through the tissue. The snare may then extend and/or rotate to drop (i.e., release) the suture from the suture manipulation device. The snare may release all or a portion of the suture.

Optionally, in Step 205, if the suture manipulation device is a different tool from the suture device, then the suture manipulation device is removed from the tissue after the suture is released from the needle. Optional Step 205 may also be performed if the suture passes back through different tissue or the same tissue but in an area proximate to the point in the tissue where the suture manipulation device passed. Further, in Step 206, a suture manipulation device is inserted in the tissue. In one or more embodiments of the invention, the suture manipulation device used to pass the suture is different from the suture manipulation device used to retrieve the suture. The suture manipulation device may be inserted in the same tissue, at a location proximate to where the suture was inserted using the suture manipulation device in Step 202. Alternatively, the suture manipulation device may be inserted in different (e.g., adjacent) tissue than the tissue through which the suture is passed by the suture manipulation device.

In Step 208, the snare of the suture manipulation device is extended. This Step 208 is performed if the snare is not already extended. The snare may be extended from the suture manipulation device using some control. The control may be manual (e.g., a user pressing a button) or automatic (e.g., the snare is released after the suture manipulation device travels ten millimeters past the tissue). Also, the control may be located on the suture manipulation device (e.g., on the handle of the suture manipulation device) or remote from the suture manipulation device (e.g., remote control).

Optionally, in Step 210, the snare is rotated. In one or more embodiments of the invention, the snare is rotated to ensnare the suture. The snare may be rotated by the base of the snare, so that the suture manipulation device itself does not rotate. The snare may also be rotated axially by turning the snare along the longitudinal and/or radial axis of the snare. The snare may also be rotated by a combination of rotations described herein and/or by other rotations known in the art. The snare may rotate in one or more full revolutions or a partial revolution. The snare may rotate clockwise or counterclockwise. The snare may be rotated from the suture manipulation device using some control. The control may be manual (e.g., a user pressing a button) or automatic (e.g., the snare is rotated one second after the snare is extended from the suture manipulation device). Also, the control may be located on the suture manipulation device (e.g., on the handle of the suture manipulation device) or remote from the suture manipulation device (e.g., remote control).

In Step 212, the suture is ensnared by the snare. If the snare is rotated, then the snare may be ensnared during the rotation of the snare. The suture may also be ensnared in one of a number of other ways. For example, a user may position the suture within the snare so that the suture becomes ensnared by the snare. As another example, the suture manipulation device (or some portion thereof) may be moved in some suitable manner as to ensnare the suture in the snare.

Optionally, in Step 214, the snare is retracted toward the suture manipulation device. Retraction of the snare toward the suture manipulation device may be partial (e.g., thirteen millimeters with further retraction possible) or full (i.e., the snare may not be retracted further). The snare may be retracted toward the suture manipulation device using some control. The control may be manual (e.g., a user pressing a button) or automatic (e.g., the snare is retracted after the snare has rotated for one full revolution). Also, the control may be located on the suture manipulation device (e.g., on the handle of the suture manipulation device) or remote from the suture manipulation device (e.g., remote control). In one or more embodiments of the invention, the suture is secured by the snare without retracting the snare toward the suture manipulation device.

In Step 216, a determination is made as to whether the suture is secured. Determining that the suture is secured may be performed manually (e.g., in sight of the user, using a viewing device (e.g., an endoscope during arthroscopic surgery)) or automatically. The determination that the suture is secured may occur automatically using one or more sensors and/or other devices adapted to make such a determination. For example, a sensor may be adapted to measure the amount of force (e.g., tension) required to retract the snare. In such a case, if the force used to retract the snare is below a threshold force, then the sensor indicates to the user that the suture is not secure and that the snare needs to be extracted and rotated again to secure the suture. Alternatively, when the force used to retract the snare is above a threshold force, the sensor may automatically extract and/or rotate the snare again to secure the suture. If the suture has not been secured, then the process reverts to Step 208. If the suture has been secured, then the process proceeds to Step 218.

In Step 218, the suture manipulation device with the suture is retracted from the tissue. The suture manipulation device may be retracted manually (as by the user) or automatically (as when using an automated process). When Step 218 is complete, the process ends.

Referring to FIG. 2B, another method for manipulating a suture in accordance with one or more embodiments of the invention is described. In Step 252, tissue is secured using a snare of a suture manipulation device. The tissue may be secured by the snare in one of a number of ways. For example, the snare may provide support for the tissue by clamping on the tissue, by providing a brace against which the tissue may rest, by providing a support to the tissue, by using some other suitable means of securing the tissue, or by using any combination thereof In one or more embodiments of the invention, the tissue is soft tissue that may move when being pierced.

In Step 254, a needle is protracted to pierce the tissue. In one or more embodiments of the invention, the needle is integrated with the same suture manipulation device as the device described above with respect to Step 252. The needle may move independently of the suture manipulation device. The distal end of the needle may include a distal end adapted to secure and/or release the suture. The needle may be protracted using some control. The control may be manual (e.g., pushing on a plunger on the handle of the suture manipulation device) or automatic (e.g., the needle is protracted three seconds after the snare secures the tissue). Also, the control may be located on the suture manipulation device (e.g., on the handle of the suture manipulation device) or remote from the suture manipulation device (e.g., remote control).

In Step 256, the suture is passed through the tissue and the snare using the needle. The distance that the suture (i.e., the distal end of the needle) passes beyond the tissue and the snare securing the tissue may vary. Further, in one or more embodiments of the invention, the suture manipulation device may be configured in such a way that the needle passes substantially close to the snare after exiting the tissue.

In Step 258, the suture is released from the needle. The suture may be released from the needle using natural forces. For example, if the needle is extended a distance (e.g., one inch) beyond the tissue and snare, friction created by elements within the body receiving the suture may be adequate to release the suture from the needle as the needle retracts. The suture may also be released from the needle using some control (e.g., release of a jam cleat). The needle may release all or a portion of the suture. The control, if any, used to release the suture from the needle may be manual (e.g., a user pressing a button) or automatic (e.g., the suture is released after the needle travels five millimeters past the tissue). Also, the control may be located on the suture manipulation device (e.g., on the handle of the suture manipulation device) or remote from the suture manipulation device (e.g., remote control).

In Step 260, the needle is retracted from the tissue. In one or more embodiments of the invention, the needle is retracted while the snare of the suture manipulation device remains substantially in place providing support to the tissue. The needle may be retracted from the tissue using some control. The control may be manual (e.g., a pulling on a plunger on the handle of the suture manipulation device) or automatic (e.g., the needle is retracted after the needle has been passed through the tissue for three seconds). Also, the control may be located on the suture manipulation device (e.g., on the handle of the suture manipulation device) or remote from the suture manipulation device (e.g., remote control).

In Step 262, the suture is ensnared with the snare. In one or more embodiments of the invention, the snare ensnares the suture as the needle is retracted. The snare may also ensnare the suture by moving the snare so that the snare is properly oriented to ensnare the suture. For example, the snare may be moved upward toward the suture to ensnare the suture.

In Step 264, a determination is made as to whether the suture is secured. Determining that the suture is secured may be performed manually (e.g., in sight of the user, using a viewing device (e.g., an endoscope during arthroscopic surgery)) or automatically. If the suture has not been secured, then the process proceeds to Step 266. If the suture has been secured, then the process proceeds to Step 268.

In Step 266, the snare is maneuvered. In one or more embodiments of the invention, the snare is maneuvered to secure the suture in the snare. After the snare is maneuvered, the process reverts to Step 264 to determine whether the maneuvering of the snare secured the suture.

In Step 268, after the suture is secured by the snare, the snare is removed with the suture. The snare may be removed in one of a number of ways. For example, the entire suture manipulation device, to which the snare is fixedly attached, may be removed. As another example, the snare (along with the rest of the suture manipulation device) may be retracted using some control. The control may be manual (e.g., pushing a button on the handle of the suture manipulation device) or automatic (e.g., the snare is protracted one second after the suture is secured). Also, the control may be located on the suture manipulation device (e.g., on the handle of the suture manipulation device) or remote from the suture manipulation device (e.g., remote control). After the snare is removed with the suture, the process ends.

Figure 3A:
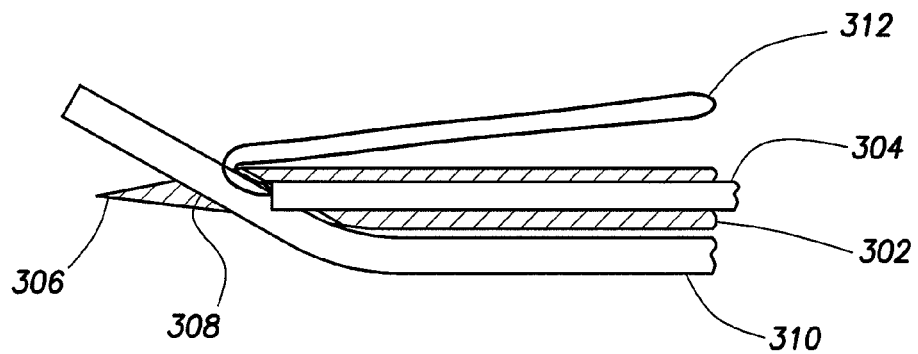
FIGS. 3A through 3D show a suturing tool with suture retrieval capability in accordance with one or more embodiments of the invention.

FIGS. 3A through 3D show a suture manipulation device with suture retrieval capability in accordance with one or more embodiments of the invention. FIG. 3A shows a cross-section of a suture manipulation device with suture retrieval capability that includes a body (302) having a cavity (314) adapted to accommodate a pushrod (304), and a needle (306) with a channel (308) adapted to allow a suture (310) to pass through. A snare (312) is attached at the distal end of the pushrod (304). Each of these components is described below. Embodiments of the invention are not limited to the configuration shown in FIGS. 3A and 3B and discussed herein.

In one or more embodiments of the invention, the suture (310) is held in place in the channel (308) of the needle (306) by the pushrod (304) when the pushrod (304) is moved toward the distal end and contacts the suture (310). The suture (310) may also be held in place in the channel (308) of the needle (306) using one or more other means that do not include use of the pushrod (304). For example, the suture (310) may be held in place by friction, as when the channel (308) is sized slightly larger than the size of the suture (310) or when extra suture (310) is threaded through the needle (306) such that, as the needle (306) is passed through tissue, both ends of the suture (310) trail the needle (306) and pass along toward the proximate end of the suture manipulation device. As another example, the suture manipulation device may include a retractable notch (e.g., a jam cleat), embedded into the body (302) at the distal end, that extends into the channel (308) to hold the suture (310) in place in the channel (308). The suture (310) may be held in place prior to and while the suture manipulation device is inserted into and passed through tissue to begin a stitch. Aside from the channel (308) in the needle (306), the suture (310) may be external to the suture manipulation device in embodiments of the invention.

In one or more embodiments of the invention, the needle (306) is used to penetrate tissue. The needle may be of any length and/or shape and may be made of any material designed to penetrate tissue and similar material so that the suture (310) may be inserted through such material. Examples of a shape of the needle (306) include, but are not limited to, straight, ¼ circle, ⅜ circle, ½ circle, ⅝ circle, compound curve, half curved (also known as ski), and half curved at both ends of a straight segment (also known as canoe). The needle (306) may also be classified, based on its point geometry. Examples of classifications of the needle (306) include, but are not limited to, taper, cutting, reverse cutting, taper cut, blunt point, and spatula point. Further, in one or more embodiments of the invention, the diameter of the needle (306) (as well as at least the portion of the body (302) that penetrates the tissue and other such material) is approximately the same as, or slightly greater than, the diameter of the suture (310).

In one or more embodiments of the invention, the pushrod (304) may be moved toward the distal end and/or the proximal end of the suture manipulation device manually (e.g., by pushing and/or pulling on a portion of the pushrod (304) extending beyond the proximal end of the body (302)), using a motorized control, using a pneumatic control, or using some other mechanism. A control used to control the position of the pushrod (304) inside the cavity (314) of the body (302) may be located at the proximal end of the body (302) (as on a handle), using a remote control device, or using some other suitable means of control. In one or more embodiments of the invention, the pushrod (304), as well as the cavity (314) of the body (302) into which the pushrod (304) resides, are circular in shape. In such a case, the pushrod (304) may be moved within the cavity (314) of the body (302) laterally and/or rotationally. The cavity (314) may be shaped in such a way as to allow the pushrod (304) to move within the cavity (314) in order to hold the suture (310) in place and/or to maneuver the snare (312) to capture the suture (310).

In one or more embodiments of the invention, when the pushrod (304) is positioned toward the distal end of the body (302) of the suture manipulation device, the snare (312) is threaded through the channel (308) in the needle (306) so that the remainder of the snare (312) (i.e., the portion of the snare (312) used to ensnare the suture) is located outside of the suture manipulation device. The base of the snare (312) may be attached to the end of the pushrod (304) at the distal end. In such a case, the base of the snare (312) may be attached to any portion of the end of the pushrod (304), including a portion that is offset from the center of the end of the pushrod (304). The snare (312) may be in one of a number of shapes, including but not limited to a closed loop and a hook.

The snare (312) may be made of one or more of a number of different materials having one or more different properties. For example, the snare (312) may be made of nitinol, a flexible metal, plastic, and/or some other suitable material. The snare (312) may have uniform or varying thicknesses throughout the length of the snare (312). Further, different portions of the snare (312) may be made of different material. For example, the base of the snare (312) attached to the end of the pushrod (304) may be made of nylon, while the rest of the snare (312) may be made of a flexible metal. The snare (312) may be of an appropriate size such that the snare (312) and the suture (310) may fit within the channel (308) at the same time.

In one or more embodiments of the invention, the body (302), the pushrod (304), and the needle (306) may be made of one or more of a number of different materials having one or more different properties. For example, the body (312) may be made of stainless steel, the pushrod (304) may be made of plastic, and the needle (306) may be made of titanium. The body (302) may have varying contours and/or features along its length. For example, toward the proximal end of the body (302), a handle may be contoured and/or made or coated with a material (e.g., rubber) to facilitate easier gripping and control by a hand using the suturing tool with suture retrieval capability. The body (302) may also include one or more control devices (e.g., button, knob) to perform functions to manipulate a suture.

Figure 3B:
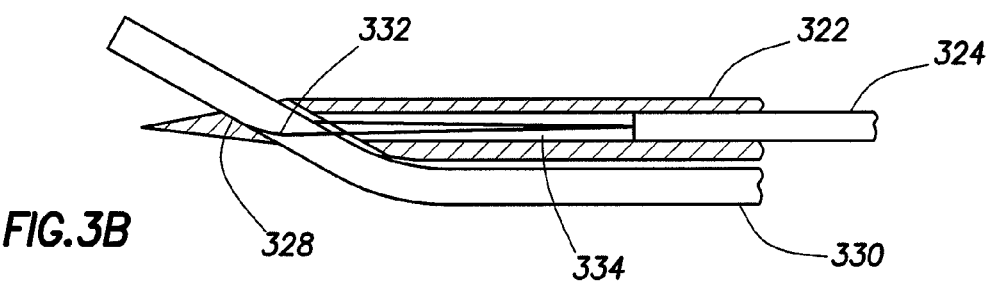

FIG. 3B shows a variation of using the suture manipulation device with suture retrieval capability as described above with respect to FIG. 3A. Specifically, when the suture manipulation device with suture retrieval capability is inserted into tissue, the suture (330) may be held securely by retracting, rather than fully inserting, the pushrod (324) within the cavity (334) of the body (322). In other words, rather than use the force of the pushrod (324) against the suture (330) in the channel (328) to hold the suture (330) in place, as described above with respect to FIG. 3A, the suture (330) may be held in place by retracting the pushrod (324) within the cavity (334) to the extent that the snare (332), attached to the end of the pushrod (324), is fully extended. Consequently, the force of the snare (332) pulling on the suture (330) toward the cavity (334) (i.e., toward the proximal end) may hold the suture (330) in place within the channel (328) of the needle (326). When the suture (330) is ready to be released for retrieval and completion of a stitch, the pushrod (324) is advanced toward the distal end so that the snare (332) slackens and no longer applies a force to the suture (330). The suture (330) may be dislodged from the channel (328) in one of a number of ways. For example, the suture manipulation device may be advanced while the suture (330) is held stationary. As a consequence, the suture (330) may slip away from the channel (328).

Figure 3C:
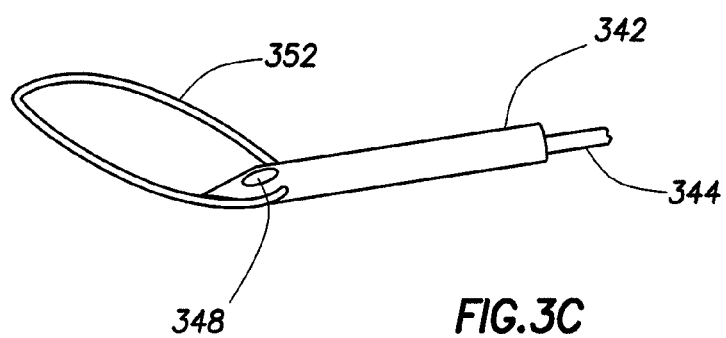

FIG. 3C shows a view of the suture manipulation device with suture retrieval capability of FIGS. 3A and 3B in accordance with one or more embodiments of the invention. In this case, the suture (not shown) has been released from the channel (348) in the body (342) of the needle. Here, the snare (352) is positioned, using the pushrod (344), to ensnare the suture for retrieval. FIGS. 4A through 4D, described below, show how the snare may be used to ensnare the suture for retrieval in accordance with one or more embodiments of the invention.

Figure 3D:
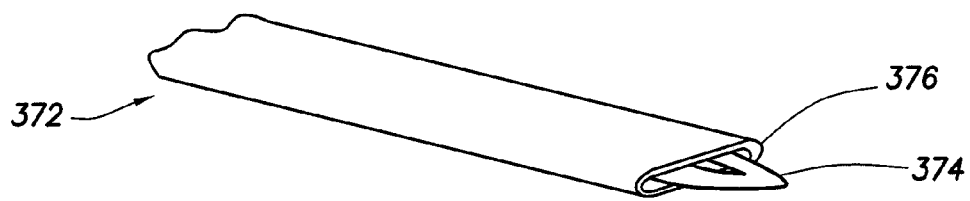
Figure 4A:
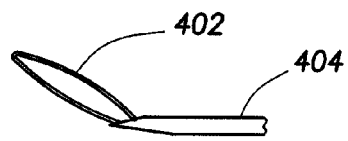
FIGS. 4A through 4D show rotating a snare in accordance with one or more embodiments of the invention.
Figure 4B:
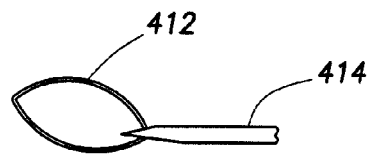
Figure 4C:
Figure 4D:
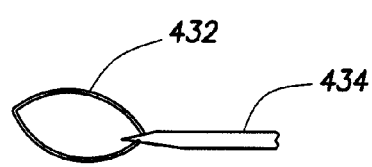

FIG. 3D shows one or more embodiments of the invention where the suture manipulation device (372) has a hollow needle, distally located, with a blunted end (376). The blunted end (376) of the suture manipulation device (372) may be slotted (e.g., a flattened tubular shape, as shown in FIG. 3D), or have some other shape with a sharp tissue-penetrating distal tip. The snare (374) in this FIG. 3D protrudes from the blunted end (376) rather than from a side-facing opening of the needle, as described for FIGS. 3A-3C above. The snare (374) may be extended from the blunted end (376) of the suture manipulation device (372) to ensnare the suture (not shown). Once the suture is ensnared, the snare (374) may be aligned (e.g., to fit in the opening at the blunted end (376)) and retracted into the suturing tool (374). The snare (374) may be controlled (e.g., extracted, protracted, rotated) using a pushrod (not shown) or other control mechanism.

In FIGS. 4A through 4D, the pushrod (not shown), the end of which the snare (e.g., 402, 412, 422, 432) is attached, is rotated so that the snare (e.g., 402, 412, 422, 432) rotates around the body (e.g., 404, 414, 424, 434) of the suture manipulation device with suture retrieval capability. The snare (e.g., 404, 414, 424, 434) may be rotated by the base of the snare (e.g., 404, 414, 424, 434), as shown in FIGS. 4A through 4D. The snare (e.g., 404, 414, 424, 434) may also be rotated in one or more other types of rotations, as described above with respect to FIG. 2A. The size of the snare (e.g., 402, 412, 422, 432) may be reduced by retracting the pushrod toward the proximal end of the suture manipulation device. Conversely, the size of the snare (e.g., 402, 412, 422, 432) may be increased by protracting the pushrod toward the distal end. Further, the angle at which the snare (e.g., 402, 412, 422, 432) creates relative to the suture manipulation device (in this example, approximately 30°) may be controlled to better ensnare the suture. For example, the entire suture manipulation device may be retracted away from the tissue and suture to decrease the angle. Conversely, the entire suture manipulation device may be protracted toward the tissue and suture to increase the angle. The angle at which the snare (e.g., 402, 412, 422, 432) creates relative to the suture manipulation device may also be controlled in a number of other ways, including but not limited to using a lever, affixed to the end of the pushrod and the base of the snare, that is adapted to push and/or pull a wire snare. The rotation of the snare (e.g., 402, 412, 422, 432) may end manually (e.g., flipping a switch, ceasing a manual operation to rotate the snare) or after the occurrence of some event (e.g., passage of time, ensnaring the suture).

Figure 5:
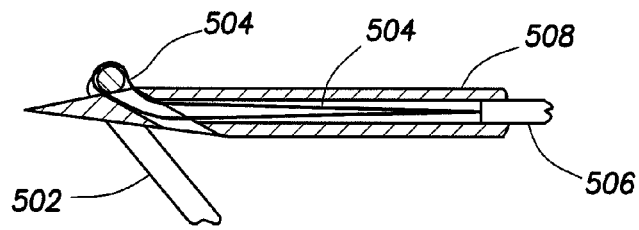
FIG. 5 shows retracting the snare in accordance with one or more embodiments of the invention.
Figure 6A:
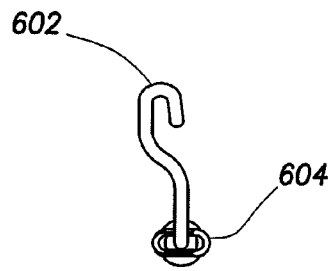
FIGS. 6A through 6D show rotating a snare in accordance with one or more embodiments of the invention.
Figure 6B:
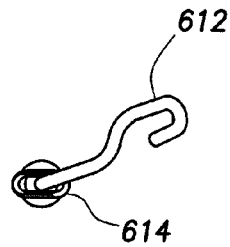
Figure 6C:
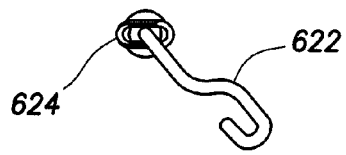
Figure 6D:
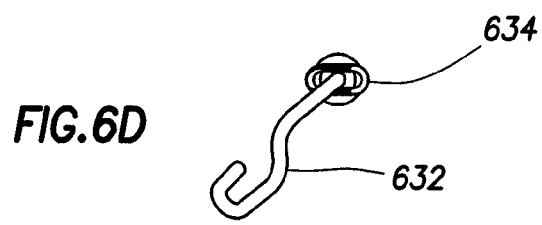

FIG. 5 shows a suture (502) that has been ensnared and secured by the snare (504) in accordance with one or more embodiments of the invention. In this case, the pushrod (506) is retracted toward the proximal end of the suture manipulation device to the point where the snare (504) is taught. The suture (502) is secured by the snare (504) against the body (508). Thus, when the pushrod (506) remains in the same position (i.e., the snare is taught), the suture manipulation device may be extracted along with the suture (502). The pushrod (506) may remain in place by use of a locking mechanism (not shown). For example, the handle (not shown) of the suture manipulation device may include a button that locks the pushrod (506) in place.

FIGS. 6A through 6D show a suture manipulation device with suture retrieval capability in accordance with one or more embodiments of the invention. In this case, the snare (e.g., 602, 612, 622, 632) is a hook. The hook may be made of thin wire, plastic, some other suitable material, or any combination thereof. The shape and size of the snare (e.g., 602, 612, 622, 632) may vary. In this case, the shape of the snare (e.g., 602, 612, 622, 632) includes a 180° arc at its distal end as well as a bend in the snare, just proximal to the 180° arc, where the lateral distance covered by the bend is equal to the diameter of the 180° arc. In other words, the end of the 180° arc aligns with the base of the snare before the bend. In one or more embodiments of the invention, the diameter of the 180° arc is slightly larger than the diameter of the suture (not shown).

In one or more embodiments of the invention, the snare (e.g., 602, 612, 622, 632) is protracted from and retracted into a slotted housing (e.g., 604, 614, 624, 634). As described above, the slotted housing (e.g., 604, 614, 624, 634) may be sized and configured in such a way as to house the snare (e.g., 602, 612, 622, 632) only when the snare is oriented in a specific manner. In one or more embodiments of the invention, the slotted housing (e.g., 604, 614, 624, 634) protrudes from the body at or near the distal end of the suture manipulation device. The pushrod may be adapted, when fully protracted inside suture manipulation device, to extend the snare (e.g., 602, 612, 622, 632) through the slotted housing (e.g., 604, 614, 624, 634) of the body in order to manipulate the snare (e.g., 602, 612, 622, 632) to ensnare the suture.

As with the loop snare described above with respect to FIGS. 3A through 5, the snare (e.g., 602, 612, 622, 632) of FIGS. 6A through 6D may rotate independent of the movement of the suture manipulation device. In this case, the snare (e.g., 602, 612, 622, 632) rotates at a relatively constant angle relative to an axis emanating perpendicular to the suture manipulation device from the base of the snare (e.g., 602, 612, 622, 632). Such an angle may be changed by moving the snare (e.g., 602, 612, 622, 632) distally or proximally within the slotted housing (e.g., 604, 614, 624, 634). In one or more embodiments of the invention, the snare (e.g., 602, 612, 622, 632) has a natural state that is bent. In such a case, retracting the snare (e.g., 602, 612, 622, 632) may reduce an amount of the bend in the snare (e.g., 602, 612, 622, 632). The snare (e.g., 602, 612, 622, 632) may rotate based on a manual instruction (e.g., a user turning a knob on the handle of the suture manipulation device), a motorized instruction (e.g., turning a switch on a remote control device), using some other suitable mechanism, or any combination thereof The rotation of the snare (e.g., 602, 612, 622, 632) may end manually (e.g., flipping a switch, ceasing a manual operation to rotate the snare) or after the occurrence of some event (e.g., passage of time, ensnaring the suture).

Figure 7A:
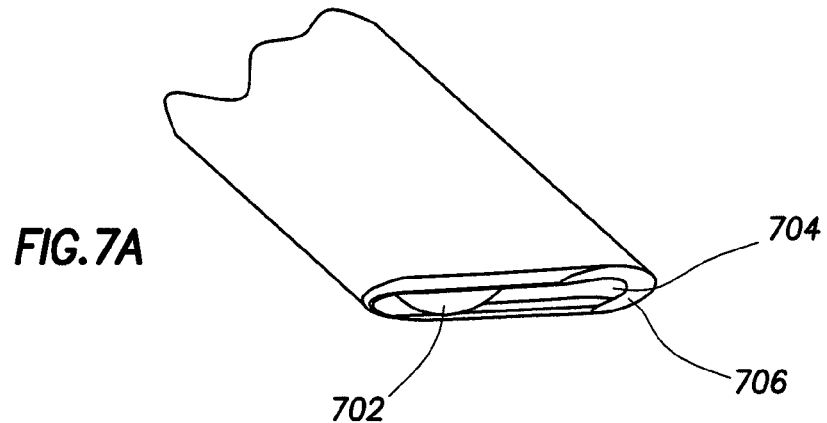
FIGS. 7A through 7D show retracting the snare in accordance with one or more embodiments of the invention.
Figure 7B:
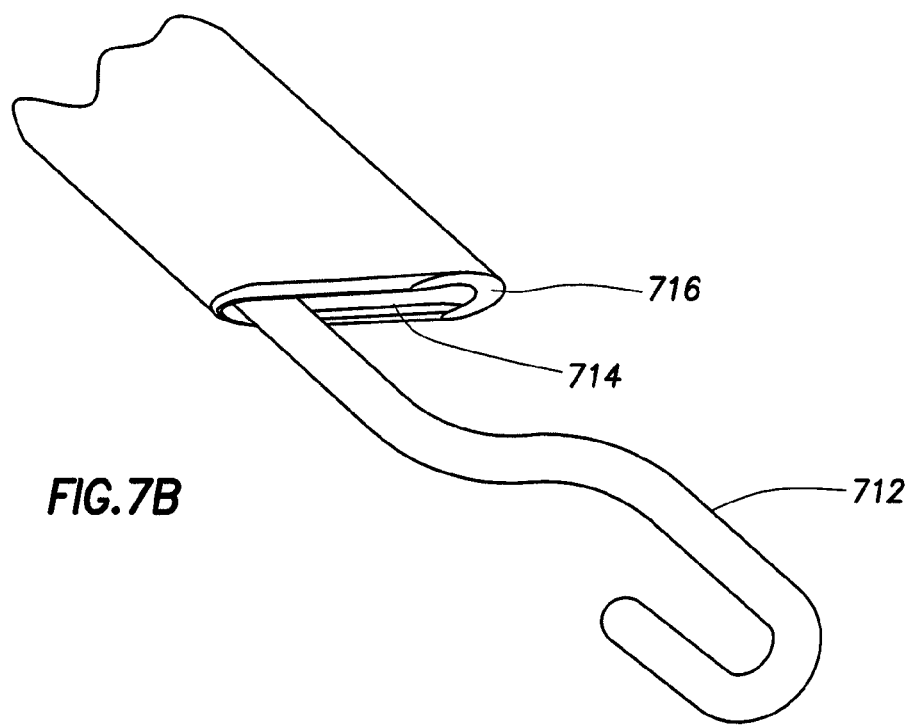

As shown in FIGS. 7A through 7D, in one or more embodiments of the invention, when the snare (e.g., 702, 712, 722, 732) is a hook or some other shape with a semi-flexible structure where the width and the height differ, a slotted housing (e.g., 704, 714, 724, 734) with the same (or slightly larger) width and height may be used. The slotted housing (e.g., 704, 714, 724, 734) may serve to hide the snare (e.g., 702, 712, 722, 732) when the suture manipulation device is passing the suture (not shown) through tissue (not shown). The slotted housing (e.g., 704, 714, 724, 734) may be configured to include a pointed tip (e.g., 706, 716, 726, 736) used to puncture the tissue and facilitate passing the suture manipulation device through the tissue. As described above, the slotted housing (e.g., 704, 714, 724, 734), when not located at the tip of the needle, may not have a pointed tip (e.g., 706, 716, 726, 736). In such a case, the slotted housing (e.g., 704, 714, 724, 734) may be located on any outer surface of the suture manipulation device As shown in FIG. 7A, the snare (e.g., 702, 712, 722, 732) may be fully retracted into the slotted housing (e.g., 704, 714, 724, 734) when the snare (e.g., 702, 712, 722, 732) is not securing the suture. By hiding the snare (e.g., 702, 712, 722, 732) at the time the suture is passed through tissue, less trauma may be caused to the tissue because the suture manipulation device has a relatively lower profile. In one or more embodiments of the invention, after the suture manipulation device passes the suture (not shown) through the tissue (not shown), the snare (e.g., 702, 712, 722, 732) is protracted out of the slotted housing (e.g., 704, 714, 724, 734) as shown in FIG. 7B. As the snare (e.g., 702, 712, 722, 732) is protracted, the snare (e.g., 702, 712, 722, 732) may be rotated, as described above with respect to FIGS. 6A through 6D, to facilitate capturing the suture.

Figure 7C:
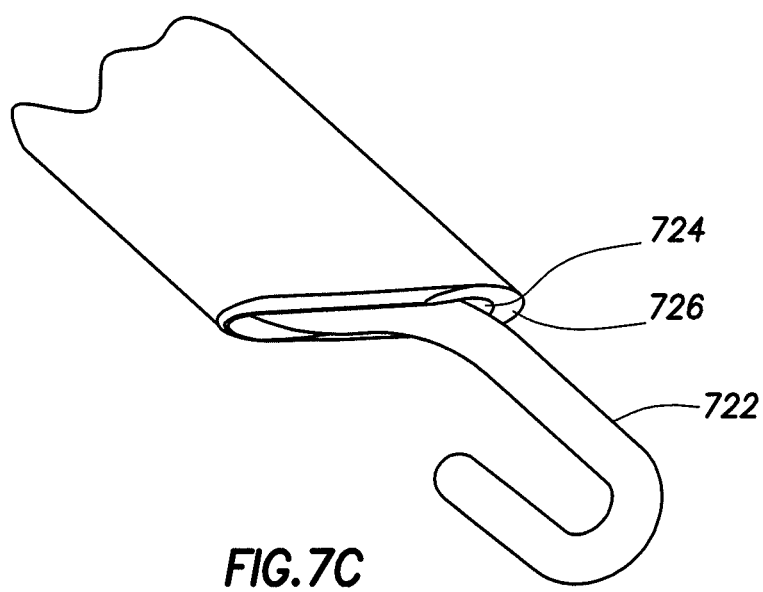
Figure 7D:
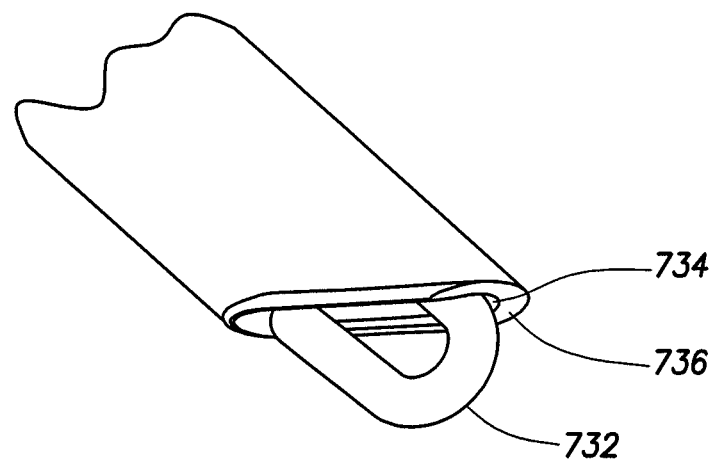

Further, when the suture is ensnared by the snare (e.g., 702, 712, 722, 732), the snare (e.g., 702, 712, 722, 732) may be retracted into the slotted housing (e.g., 704, 714, 724, 734) as shown in FIGS. 7C and 7D. Because of the dimensions of the slotted housing (e.g., 704, 714, 724, 734), retracting the snare (e.g., 702, 712, 722, 732) into the slotted housing (e.g., 704, 714, 724, 734) may only occur if the snare (e.g., 702, 712, 722, 732) is properly oriented with respect to the slotted housing (e.g., 704, 714, 724, 734). Further, as shown in FIG. 7D, when the snare (e.g., 702, 712, 722, 732) is retracted into the slotted housing (e.g., 704, 714, 724, 734), the snare (e.g., 702, 712, 722, 732) may protrude slightly beyond the slotted housing (e.g., 704, 714, 724, 734). The snare (e.g., 702, 712, 722, 732) may protrude because the suture (not shown), when secured by the snare (e.g., 702, 712, 722, 732), may be wedged between the walls of the slotted housing (e.g., 704, 714, 724, 734) and the snare (e.g., 702, 712, 722, 732), preventing he snare (e.g., 702, 712, 722, 732) from fully retracting. In other words, the snare (e.g., 702, 712, 722, 732) may be substantially retracted, as shown in FIG. 7D, rather than fully retracted when the suture is secured by the snare (e.g., 702, 712, 722, 732).

Figure 8:
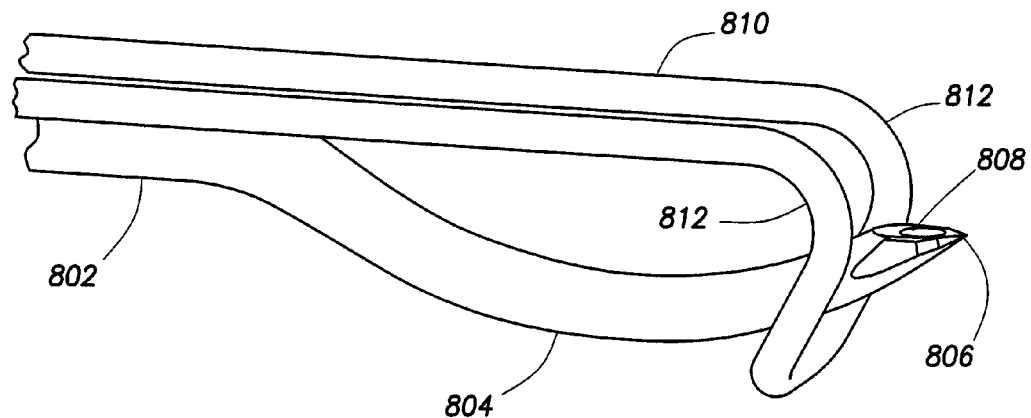
FIG. 8 shows an example of a suturing tool with suture retrieval capability in accordance with one or more embodiments of the invention.

FIG. 8 shows a suture manipulation device with suture retrieval capability in accordance with one or more embodiments of the invention. The suture manipulation device of FIG. 8 includes a needle (802) that may be curved at the distal end (804), and a tip (806) with a penetrating point and means to hold and release suture (not shown) after passing the suture. In this case, the means to pass the suture is a slot (808) through the tip (806) that is large enough to allow the suture to pass. The tip (806) may include a mechanism (e.g., rollers, a retractable and flexible pushrod in a channel inside the needle (802), a mechanically-operated jam cleat inside the slot (808)) that allows a user to secure and/or release the suture.

The suture manipulation device may also include a suture retriever (810). In one or more embodiments of the invention, a snare (812) located at the distal end of the suture retriever (810) is adapted to secure tissue in addition to retrieve a suture. The snare (812) of the suture retriever (810) may secure tissue by clamping on the tissue, providing a brace against which the tissue may rest, providing a support to the tissue, using some other suitable means of securing the tissue, or any combination thereof In one or more embodiments of the invention, the snare (812) of the suture retriever (810) may secure tissue so that the needle (802) may pierce the tissue without tissue migration away from the penetration of the needle (802).

As shown in FIG. 8, the suture retriever (810) is two parallel rods, and the snare (812) of the suture retriever (810) is a semi-circular loop connecting the two rods and bent at some angle that is approximately perpendicular to the needle (802) as the needle (802) finishes passing through the tissue. In this case, the snare (812) is bent relative to the two parallel rods of the suture retriever (810) so that the angle formed between the snare (812) and the needle (802), as the needle (802) bridges the snare (812), is approximately 110°, thus making passage into the tissue easier. In general, embodiments of the invention may be configured so that the angle between the snare (812) and the needle (802) may vary. For example, the snare (812) and/or the needle (812) may be adjusted to change the angle between the snare (812) and the needle (812). The angle between the snare (812) and the needle (812) may range from slightly above 0° to 180°.

Under the configuration as shown in FIG. 8, the snare (812) of the suture retriever (810) is adapted to secure a top and/or back side of tissue as the needle (802) penetrates the tissue. Further, the snare (812) of the suture retriever (810) may be configured to ensnare and/or secure the suture. For example, the snare (812) may be tapered so that the suture becomes wedged in the snare (812). As another example, the snare (812) may include a latching mechanism that allows the suture to pass toward the loop in the snare (812) and remain secured until the latching mechanism is released, either by the user or automatically (e.g., once the suture manipulation device is removed a certain distance from the tissue).

The needle (802) may be attached at the proximal end to a body (not shown) and/or handle (not shown) of the suture manipulation device. In one or more embodiments of the invention, the needle (802) may be extended and retracted relative to the suture retriever (810). In other words, when the suture retriever (810) is held in place behind tissue, the needle (802), with suture, may be extended distally to penetrate the tissue. Further, the needle (802) may extend beyond the snare (812) of the suture retriever (810). Specifically, as the distal end (e.g., (806), (808)) of the needle (802) is advanced beyond the snare (812) of the suture retriever (810), the distal end (e.g., (806), (808)) of the needle (802) (including the suture) passes between the two rods and above the semicircular loop connecting the two rods of the snare (812) of the suture retriever (810). When the needle (802) has been extended far enough through the tissue, the suture may be released (as described above) and the needle (802) retracted back through the tissue without some or all of the suture. Alternatively, the suture may be pushed well beyond the snare (812) but not released. The needle may then be retracted from the tissue followed by the suture retriever (810). The suture retriever (810), as it is retracted, may ensnare and secure the suture, folded over the snare (812). In one or more embodiments of the invention, the suture is ensnared by the snare (812) when the suture is released from the needle (802).

Continuing with FIG. 8, when the suture has been released from the needle (802), the suture retriever (810) may retrieve the suture. In one or more embodiments of the invention, the suture retriever (810) may not retrieve the suture until the needle (802) is withdrawn from the tissue. The suture may be retrieved using the suture retriever (810) using a manual and/or automatic process. A manual process for retrieving a suture may involve actions by a user. For example, the user may manually retrieve a suture by retracting the needle (802), lifting the suture manipulation device (and thus the suture retriever (810)) upward and away from the tissue so that the suture ensnares and secures the snare (812) of the suture retriever (810), and removing the suture manipulation device (and thus the suture). Some or all of this process may also be performed automatically using one or more controls.

In one or more embodiments of the invention, the needle (802) and the suture retriever (810) (or portions thereof) of the suture manipulation device may rotate independently. The needle (802) and the suture retriever (810) (or portions thereof) may also rotate in tandem. Further, the needle (802) and/or the suture retriever (810) (or portions thereof) may be keyed, as described above, to assist with orienting the needle (802) and/or the suture retriever (810) (or portions thereof) when protracting and/or extracting the needle (802) and/or the suture retriever (810) (or portions thereof).

The following description (in conjunction with FIGS. 2A through 8) describes a number of examples in accordance with one or more embodiments of the invention. The examples are for explanatory purposes only and are not intended to limit the scope of the invention. Terminology used in FIGS. 2A through 8 may be used in the examples without further reference to FIGS. 2A through 8.

EXAMPLE 1

Figure 9A:
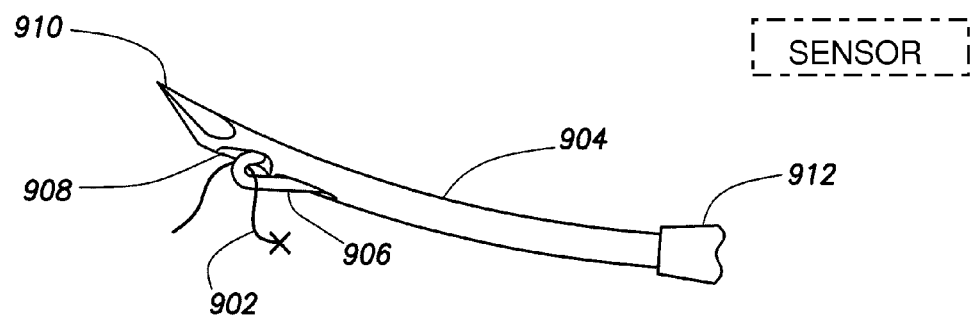
FIGS. 9A through 10B show an example of retrieving a suture in accordance with one or more embodiments of the invention.

Consider the following example, shown in FIGS. 9A through 10B, which describes using a single suture manipulation device to pass suture and retrieve the suture in accordance with one or more embodiments described above, particularly as described above with respect to FIG. 2A and FIGS. 6A through 7D. In this example, as shown in FIG. 9A, consider the scenario in which suture (902) is secured to the needle (904) of a suture manipulation device by a snare (906). Here, the needle (904) has a penetrating point (910) at the distal end for penetrating tissue. The proximal end of the needle (904) is connected to the body (912) of the suture manipulation device. The snare (908) in this example is a hook and is retracted into a channel (not shown) running inside the length of the needle (904) through a female housing (908), located in the side of the needle (904) below the distal end, to secure the suture (902). The female housing (908) may be configured to allow little, if any, of the snare (906) to protrude beyond the wall of the needle (904) when the snare (906) is fully retracted.

Figure 10B:
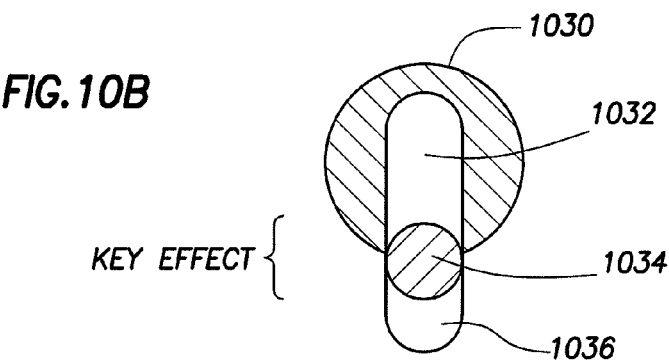
Figure 10A:
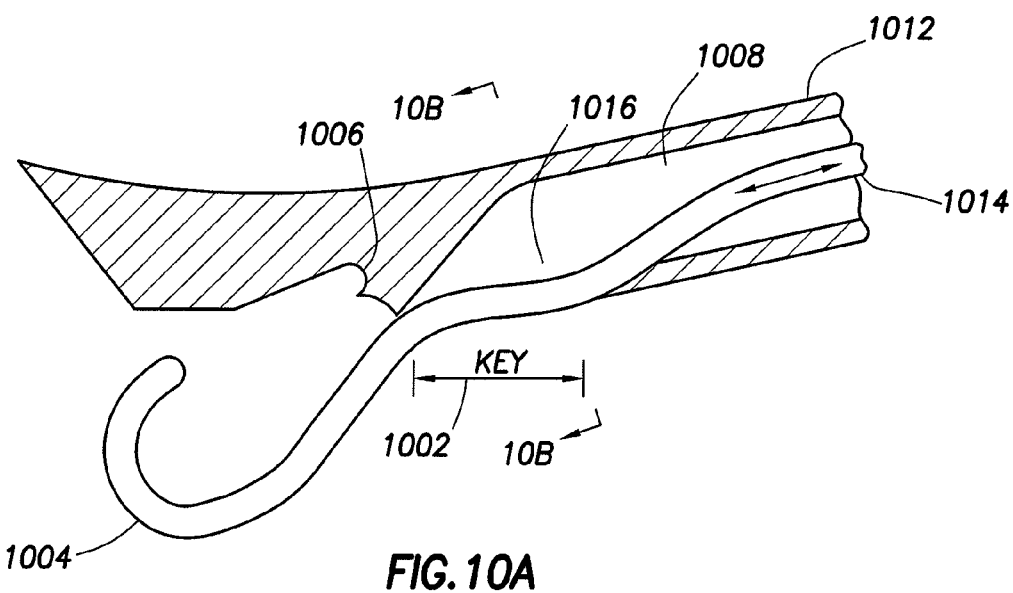

The snare (906) and/or the female housing (908) in the side of the needle (904) may be configured in one of a number of ways to seat the snare (906) flush or nearly flush with the outer side of the needle (904) when the snare (906) is fully retracted. An example of how the snare (906) and the female housing (908) may be configured, in accordance with one or more embodiments of the invention, is shown in FIGS. 10A and 10B. Specifically, in FIG. 10A, the snare (1014) is configured as a hook (1004) at the distal end and includes a key (1002) proximate to the hook (1004). The key (1002) may be a section of the snare (1014) that is created by a bend in the snare on either side of the key (1002). The key (1002) may be of any length. For example, as shown in FIG. 10A, the length of the key (1002) may be approximately equal to the length of the opening (1016) of the channel (1008) to the side of the needle (1012). As another example, the length of the key (1002) may be less than the length of the opening (1016) of the channel (1008) to the side of the needle (1012). The key (1002) may be used to secure the snare (1014) when the snare (1014) is in a retracted position. The key (1002) may also be used to ensure that the snare (1014) is properly oriented (e.g., the opening of the hook (1004) at the distal end of the snare (1014) faces the female housing (1006) of the needle (1012)) when being retracted.

A cross section of the key is shown in FIG. 10B. Specifically, the needle (1030) is shown to enclose the channel (1032), which in turn encloses most of the snare. The key (1034) of the snare, positioned at the opening of the channel (1032) on the side of the needle (1030), separates the snare proximal to the key (1034) within the channel (1032), and the snare distal to the key (1034) outside of the channel (1032) and needle (1030). As the snare is retracted within the channel (1032) toward the proximal end of the needle, the key (1034) helps secure the snare in a retracted position. As seen in FIG. 10B, a portion of the hook (1036) may protrude slightly from the outer edge of the needle (1030). In one or more embodiments of the invention, the key prevents rotational movement of the snare while allowing translation (e.g., protraction, retraction) of the snare.

Continuing with FIG. 10A, the needle (1012) is further configured to include a female housing (1006). Specifically, the female housing (1006) may be shaped to complement the hook (1004) of the snare (1014), so that when the snare (1014) is full retracted, the hook (1004) sits inside the female housing (1006) so that little or no part of the hook (1004) protrudes beyond the perimeter of the needle (1012). In one or more embodiments of the invention, the closer the key is located to the hook (1004), the more effective the key (1004) operates to properly orient (e.g., fit the hook (1004) into the female housing (1006)) the hook (1004) as the hook (1004) is retracted. In one or more embodiments of the invention, the female housing (1006) may limit the amount that the hook (1004) may be retracted so that a suture captured between the hook (1004) and the needle (1012) may slide with minimal friction.

Figure 9B:
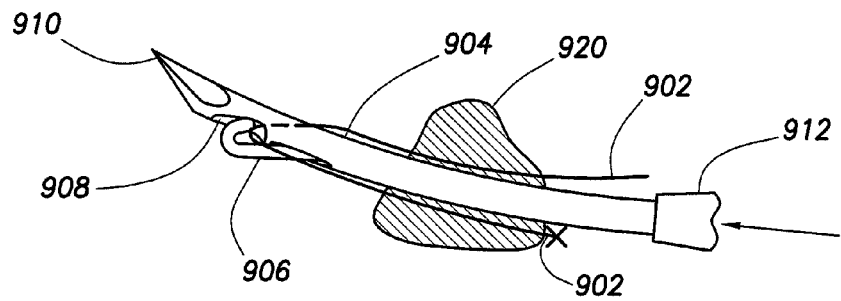

Continuing with Example 1, FIG. 9B shows the suture manipulation device after it has penetrated the tissue (920). The penetrating point (910) of the needle (904) is used to pierce the tissue (920) and create an opening through which the rest of the needle (904) may traverse. Further, the suture (902) remains secure as the needle (904) travels through the tissue (920) because the snare (906) remains retracted. Consequently, the suture has gone through the tissue along with the needle (904) and the snare (906).

Figure 9C:
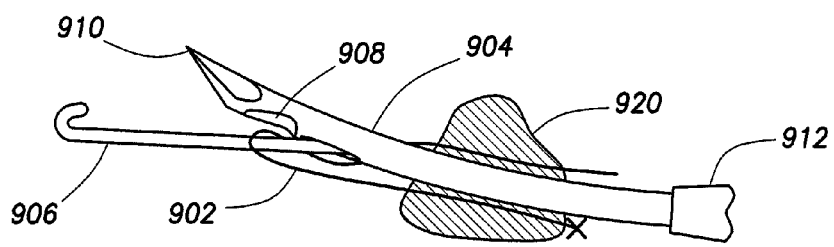

In FIG. 9C, the snare (906) is extended from the female housing (908) and the needle (904). The snare (906) may be extended using some control (manual or automatic) for the device. Further, the snare (906) may rotate while the snare (906) is extended and/or after the snare (906) has been extended. The snare (906) may rotate in one or more full revolutions or a partial revolution. The snare (906) may rotate clockwise or counterclockwise. A user may control one or more rotational movements of the snare (906) and/or the rotational movements may occur automatically once the snare (906) begins to extend. As the snare (906) is extended, the suture (902) is released from the snare (906).

Figure 9D:
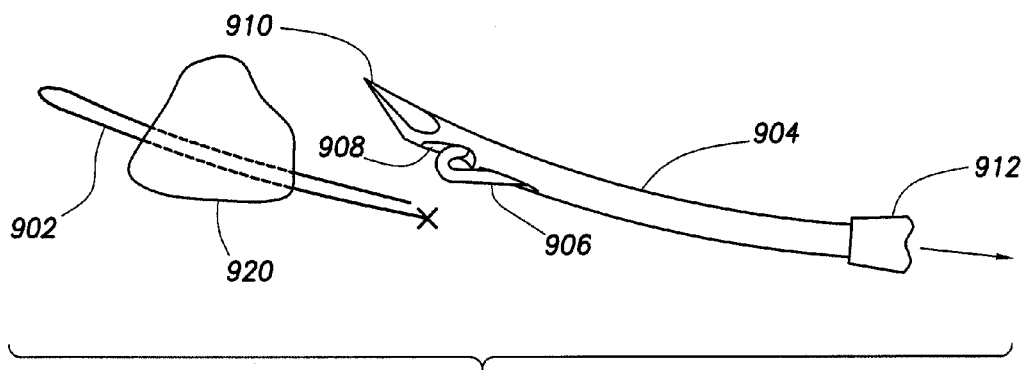

In FIG. 9D, the snare (906) is retracted without the suture (902). When the snare (906) is retracted, the suture manipulation device is removed by being pulled back through the tissue (920). As the suture manipulation device is removed from the tissue (920), the suture (902) remains threaded through the tissue (920).

Figure 9E:
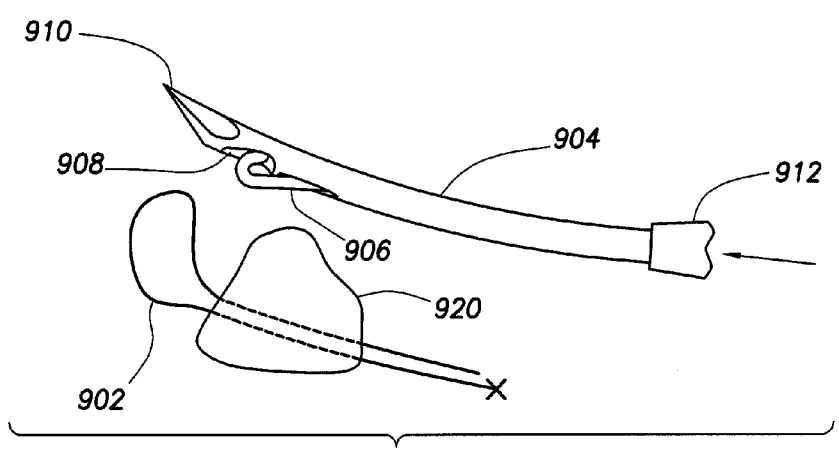

In FIG. 9E, the suture manipulation device is positioned into a different location. Specifically, the needle (904) may penetrate the tissue (920) at a location adjacent to the location in the tissue (920) where the previous penetration occurred. Alternatively, the needle (904) may penetrate different tissue (not shown) that is proximate to the tissue (920). As another alternative, the needle (904) may be positioned in a location that does not penetrate any tissue (e.g., tissue (920)) but that is proximately located to the suture (902) awaiting retrieval. As the needle (904) penetrates tissue (e.g., tissue (920)) or is positioned proximate to the tissue (920), the snare (906) may remain retracted. In one or more embodiments of the invention, the needle (904) is protracted to a point such that the snare (906), when extended, may retrieve the suture (902).

Figure 9F:
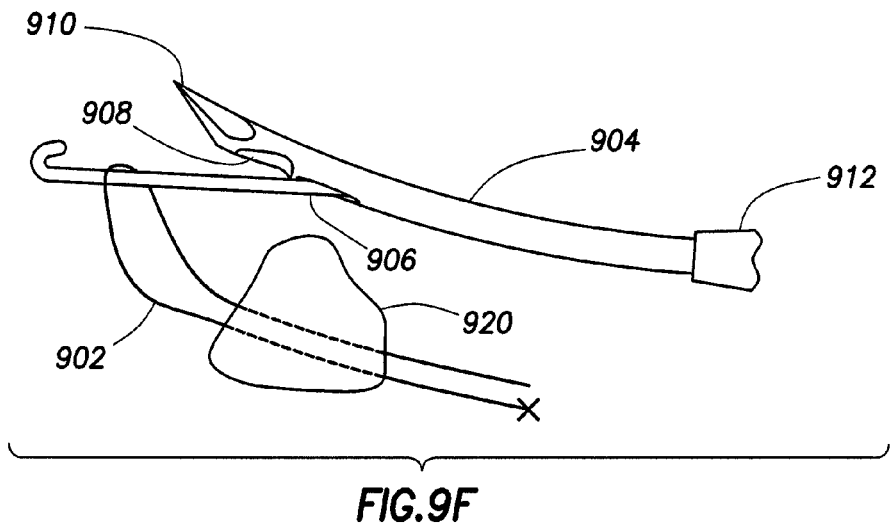

In FIG. 9F, the snare (906) is extended from the female housing (908) and the needle (904). In this case, the snare (906) is extended and rotated to ensnare the suture (902). When the suture (902) is ensnared by the snare (906), the snare (906) is retracted. When the snare (906) is retracted into the female housing (908), the suture (902) is secured. Alternatively, the snare (906) may remain extended (as shown in FIG. 9F) relative to female housing (908).

Figure 9G:
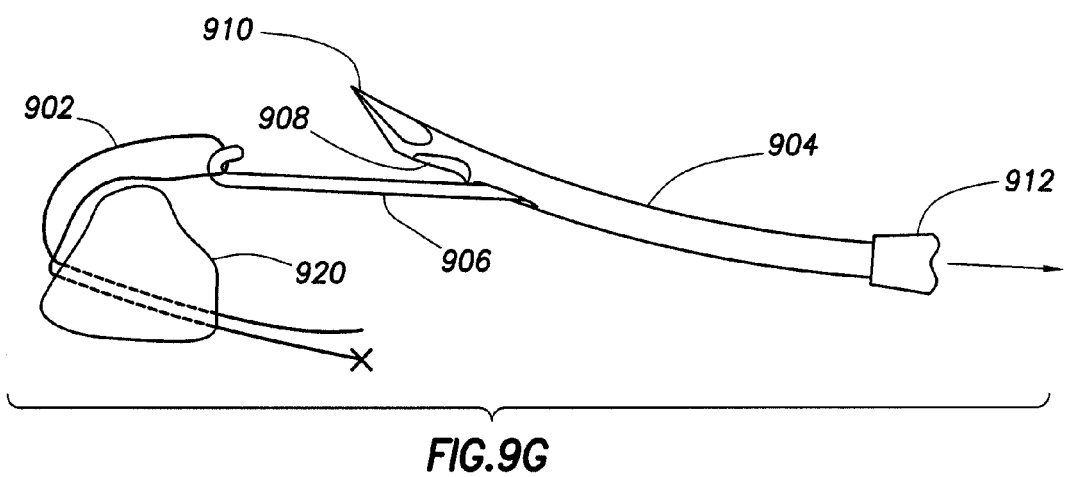

In FIG. 9G, once the suture (902) is secured, the needle (904) is removed.

In one of more embodiments of the invention, as the needle (904) is removed, a stitch is made with the suture (902). The entire suture manipulation device may then be retracted, bringing the suture (902) with the suture manipulation device. When the suture manipulation device is removed, the snare (906) may remain extended, as shown in FIG. 9G. Alternatively, the snare (906) may be retracted when the suture manipulation device is removed.

EXAMPLE 2

Figure 11A:
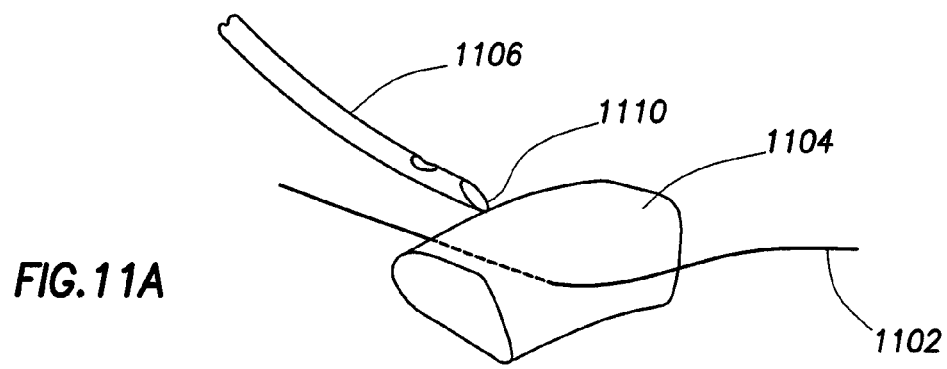
FIGS. 11A through 11H show an example of retrieving a suture in accordance with one or more embodiments of the invention.
Figure 11B:
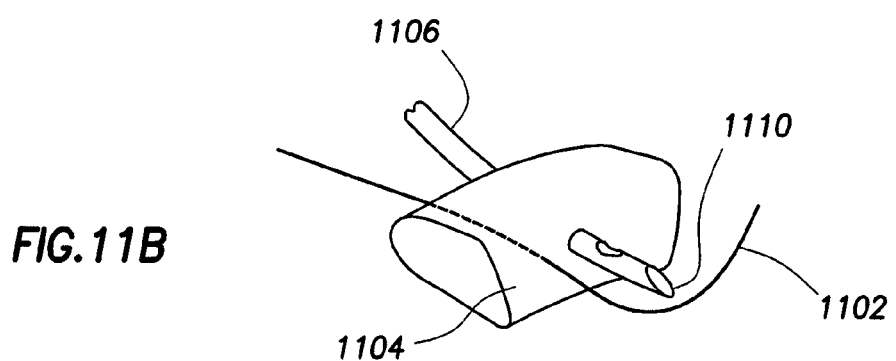

Consider the following example, shown in FIGS. 11A through 11H, which describes retrieving a suture using a suture manipulation device in accordance with one or more embodiments described above, particularly as described above with respect to FIG. 2A and FIGS. 6A through 7D. In this example, consider the scenario in which suture (1102) is inserted into tissue (1104), as shown in FIG. 11A. The suture (1102) is retrieved to create a stitch. To retrieve the suture (1102), a suture retrieving device (1106), in accordance with one or more embodiments of the invention, is used. As shown in FIG. 11B, the needle (1110) of the suture retrieving device (1106) is inserted into the tissue (1104) in an area proximate to where the stitch is desired.

Figure 11C:
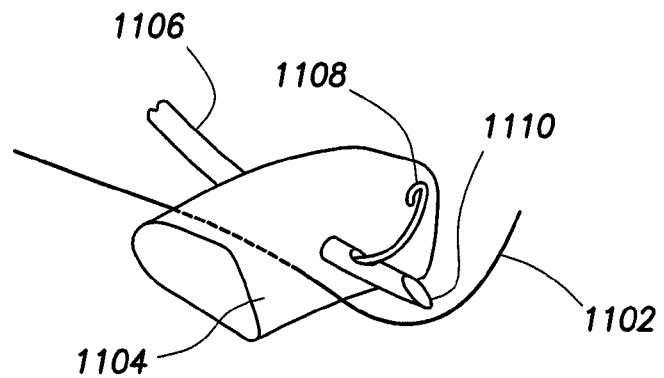

Once the needle (1110) of the suture retrieving device (1106) is inserted far enough through the tissue (1104), the snare (1108) is extended from the suture retrieving device (1106), as shown in FIG. 11C. In this example, the snare (1108) protruded near the proximal end, but not at the needle of, the suture retrieving device (1106). Further, the snare (1108) used in this example is in the shape of a hook. A slotted opening (not shown) may be used for the snare (1108) in this example.

Figure 11D:
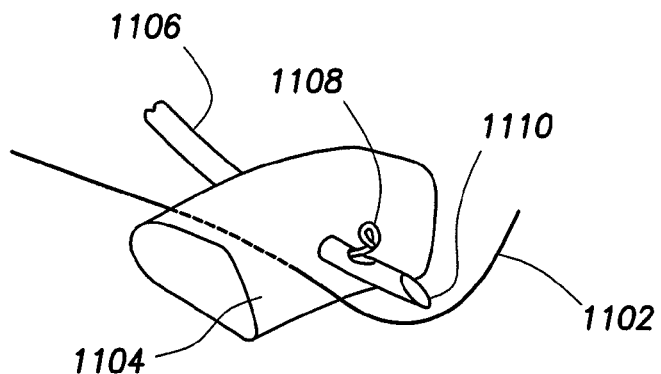
Figure 11E:
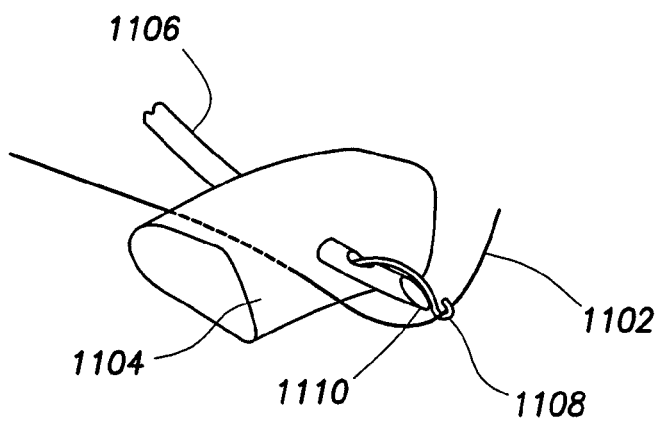
Figure 11F:
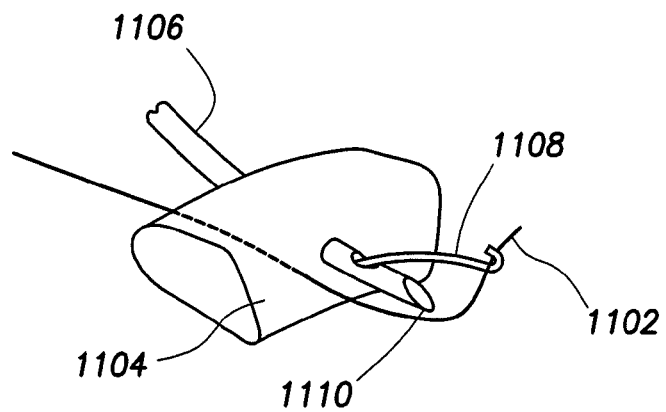

Once the snare (1108) is extended from the suture retrieving device (1106), the snare (1108) is rotated in order to ensnare the suture (1102), as shown in FIGS. 11D through 11F. In this example, the snare (1108) is rotated in a clockwise direction as viewed by the user. In other words, the snare (1108) is swept in the direction of the opening of the hook so that the hook may ensnare the suture (1102).

Figure 11G:
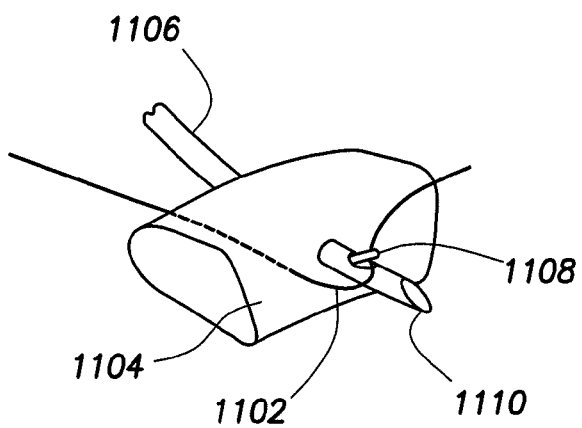

When the rotation of the snare (1108) captures the suture (1102), the snare (1108) is retracted into the suture retrieving device (1106), as shown in FIG. 11G. As the snare (1108) retracts, it brings the suture (1102) toward the suture retrieving device (1106). When the snare (1108) is completely retracted, the suture (1102) is secured against the suture retrieving device (1106).

Figure 11H:
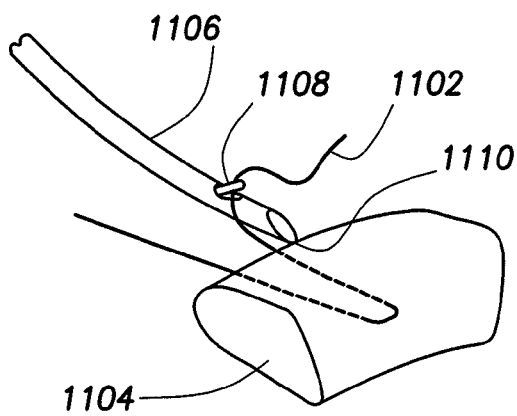

As shown in FIG. 11H, the suture retrieving device (1106), along with the suture (1102), is then retracted through the tissue (1104). Once the suture retrieving device (1106) is fully removed from the tissue (1104), the stitch may be completed.

EXAMPLE 3

Consider the following example, shown in FIGS. 12A through 12D, which describes retrieving a suture using a suture manipulation device in accordance with one or more embodiments described above, particularly as described above with respect to FIGS. 2B and 8. Consider the scenario in which a stitch is made using suture (1212) passed through tissue (1206) that requires support to be held in place. Initially, in FIG. 12A, the tissue (1206) is secured using a snare (1210) located at the distal end of a suture retriever (1208). Specifically, the distal end is placed behind the tissue (1206) that is being penetrated. For purposes of this example, the components of the suture manipulation device are configured as described above with respect to FIG. 8.

Figure 12A:
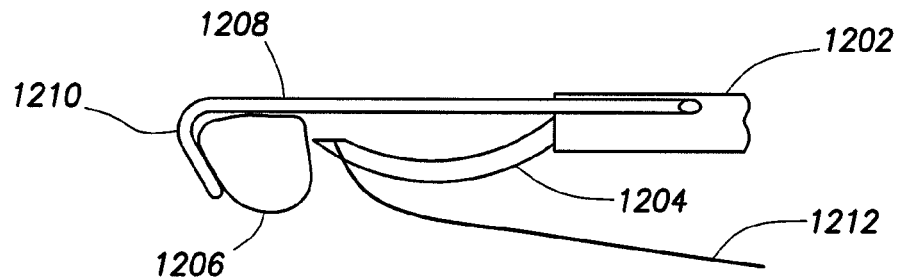
FIGS. 12A through 12D show an example of retrieving a suture in accordance with one or more embodiments of the invention.
Figure 12B:
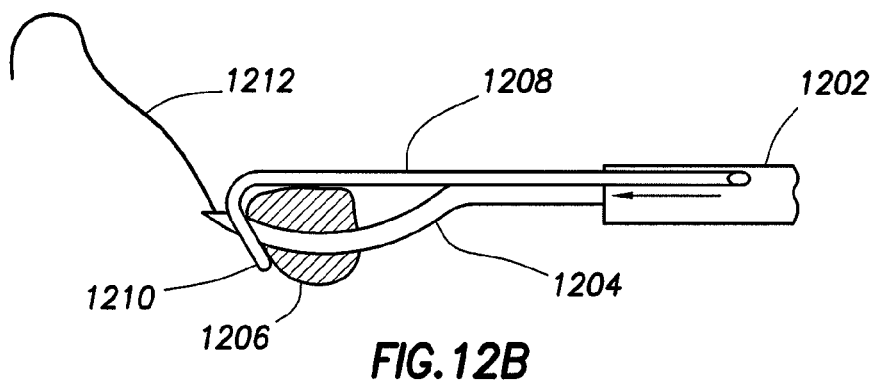

Once the tissue (1206) is secured using the snare (1210) of the suture retriever (1208), the needle (1204) is used to pass the suture (1212) through the tissue (1206), as shown in FIG. 12B. In this example, the needle (1204) is advanced through the tissue (1206) while the suture retriever (1208) and the body (1202) remain in a substantially fixed position relative to the tissue (1206). The tissue (1206) is held in place by the snare (1210) of the suture retriever (1208) as the needle (1204), along with the suture (1212), penetrates and passes through the tissue (1206). In this example, the distal end of the needle (1204) is advanced beyond the snare (1210) of the suture retriever (1208). Further, as the distal end of the needle (1204) is advanced beyond the snare (1210) of the suture retriever (1208), the distal end of the needle (including the suture (1212)) passes between the two rods and above the semi-circular loop connecting the two rods of the snare (1210) of the suture retriever (1208). When the needle (1204) (as well as the suture (1212) manipulated by the needle (1204)) is passed far enough beyond the tissue (1206), the suture (1212) is released from the needle (1204).

Figure 12C:
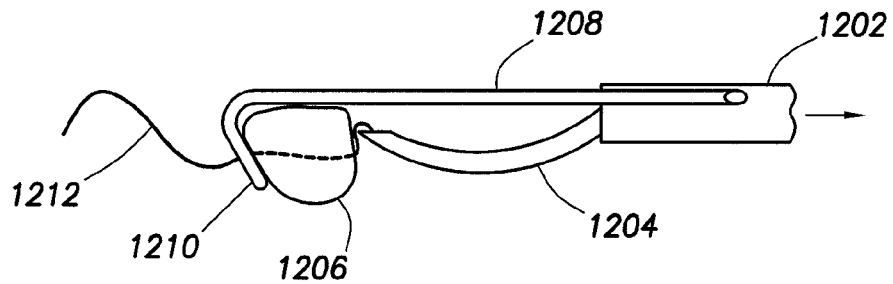

After the suture (1212) is released from the needle (1204), the needle (1204) is retracted through the tissue (1206), as shown in FIG. 12C. Similar to protracting the needle (1204), as described above with respect to FIG. 12B, the body (1202) and the suture retriever (1208) may remain in a substantially fixed position relative to the tissue (1206) as the needle (1204) is retracted out of the tissue (1206) and into the body (1202).

Figure 12D:
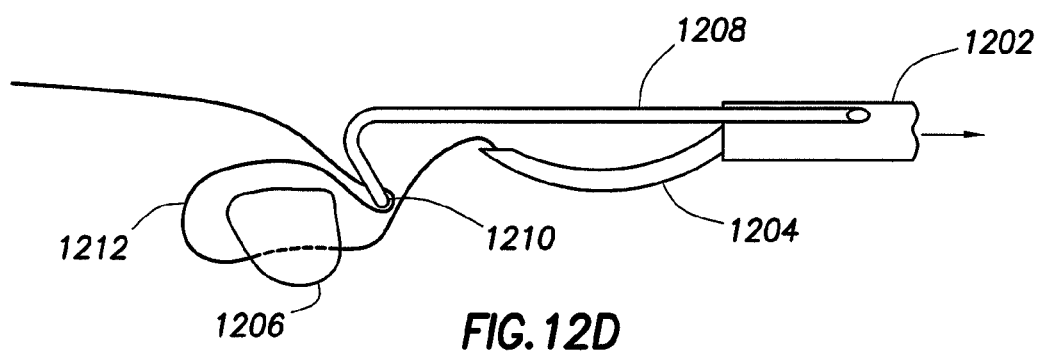

Once the needle (1204) is retracted enough (e.g., fully retracted into the body (1202), completely clear of the tissue (1206)), the suture retriever (1208), using the snare (1210), ensnares and secures the suture (1212), as shown in FIG. 12D. The suture (1212) may be ensnared in the snare (1210) in one of a number of ways. In this example, the snare (1210) is lifted to clear the tissue (1206), which also ensnares the suture (1212) between the two rods and the semi-circular loop that connects the two rods in the snare (1210). The snare (1210) may be lifted by lifting and/or tilting the body (1202). When the suture (1212) is secured in the snare (1210), then the entire device is removed.

One or more embodiments of the invention provide for manipulating a suture. Specifically, embodiments of the invention allow a user to more efficiently push and/or retrieve a suture to create one or more stitches in tissue. Creating accurate stitches in tissue may be a time-consuming process because of the size of the instruments (e.g., suture, needle, suture retrieving device) used and/or because of the small space in which to work to create stitches in the tissue. Embodiments of the invention may reduce the amount of time spent by the user and increase the accuracy of the stitches created by the user.

In embodiments of the invention, the user may be a surgeon, nurse, technician, doctor, veterinarian, or other similar professional creating stitches in tissue to close a wound. Embodiments of the invention may allow a user to secure tissue from migrating or moving away when the tissue is pierced to pass a suture. Embodiments of the invention may also eliminate the need to use a separate instrument to retrieve the suture after the suture has passed through the tissue. Embodiments of the invention may also eliminate the need to use a separate backing device (e.g., bone) to provide stability to soft tissue as the tissue if pierced. Embodiments of the invention may also automatically capture the suture as the suture is passed through the tissue.

Further, embodiments of the invention may allow a suture to be passed through tissue with a suture manipulation device having a minimal diameter (1.0 mm or less). Currently, instruments of approximately 2.5 mm in diameter are used to manipulate suture through tissue. Embodiments of the invention also provide the advantage of incorporating a suture pusher and a suture retriever into a single instrument or device. Embodiments of the invention also provide the advantage of a retractable snare that is adapted to ensnare and secure the suture for retrieval. Rotating the snare in one or more rotational directions allows embodiments of the invention to more easily and efficiently ensnare and secure the suture for retrieval.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A suture manipulation device comprising:
    a body;
    a snare operatively connected to the body and adapted to:
        protract from the body through an opening in the body;
        ensnare a portion of suture passed through tissue;
        secure the portion of the suture; and
        wherein the snare includes, at a distal end, a hook; and
    a slot located distally in the body and adapted to receive the hook to prevent the snare from retracting into the body through the opening in the body, wherein the slot is separate and distinct from the opening in the body.

2. The suture manipulation device of claim 1, wherein the body has a length and comprises:
    a shaft located inside the body and running proximally along the length of the body; and
    a needle at a distal end of the body adapted to:
    secure the portion of the suture;
    pierce the tissue; and
    release, after piercing the tissue, the portion of the suture.

3. The suture manipulation device of claim 2, wherein the needle is curved.

4. The suture manipulation device of claim 2, wherein the needle releases the portion of the suture before the portion of the suture is ensnared by the snare.

5. The suture manipulation device of claim 2, wherein the needle comprises an angled slot forming a cavity large enough to allow the portion of the suture to pass.

6. The suture manipulation device of claim 2, wherein the slot is located at a distal end of the needle.

7. The suture manipulation device of claim 1, wherein the snare comprises a wire having a thickness and a bend proximal to the hook.

8. The suture manipulation device of claim 1 wherein the hook is substantially retracted into the slot when securing the portion of the suture.

9. The suture manipulation device of claim 8, wherein the slot is located along the length of the body.

10. The suture manipulation device of claim 1, wherein the snare is further adapted to rotate, after protracting from the body, independent of the body and to ensnare the portion of suture passed through tissue while rotating.

* * * * *